(12) United States Patent
Cunningham et al.

(10) Patent No.: US 6,688,158 B2
(45) Date of Patent: Feb. 10, 2004

(54) FLEXURAL PLATE WAVE SENSOR AND ARRAY

(75) Inventors: Brian T. Cunningham, Lexington, MA (US); John R. Williams, Lexington, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 10/241,347

(22) Filed: Sep. 11, 2002

(65) Prior Publication Data

US 2003/0066348 A1 Apr. 10, 2003

Related U.S. Application Data

(62) Division of application No. 09/531,970, filed on Mar. 20, 2000, now abandoned.

(51) Int. Cl.[7] ............................ G01N 29/02; H01L 21/02
(52) U.S. Cl. ..................... 73/24.06; 73/61.75; 422/69; 438/49
(58) Field of Search .................... 73/24.06, 24.01, 73/61.49, 61.75, 64.53; 310/322; 422/69; 438/48, 49, 50, 456

(56) References Cited

U.S. PATENT DOCUMENTS

| | | | | |
|---|---|---|---|---|
| 5,189,914 A | * | 3/1993 | White et al. | 73/24.06 |
| 5,836,203 A | * | 11/1998 | Martin et al. | 73/24.06 |

* cited by examiner

Primary Examiner—John E. Chapman
(74) Attorney, Agent, or Firm—Iandiorio & Teska

(57) ABSTRACT

A method for manufacturing a flexural plate wave sensor including the steps of depositing a sacrificial material layer over a silicon substrate, depositing a membrane layer over the sacrificial material layer with the membrane layer covering the sacrificial material layer and contacting the silicon substrate, depositing a piezoelectric layer over the membrane layer, forming a first transducer on the piezoelectric layer, forming a second transducer on the piezoelectric layer, spaced from the first transducer, removing the sacrificial material layer to expose a portion of the membrane layer, and depositing an absorptive coating on the exposed portion of the membrane layer.

8 Claims, 12 Drawing Sheets

FLEXURAL PLATE WAVE SENSOR AND ARRAY

RELATED APPLICATIONS

This application is a divisional application of U.S. patent application Ser. No. 09/531,970 filed Mar. 20, 2000, now abandoned, hereby incorporated herein by reference.

FIELD OF THE INVENTION

This invention relates generally to a flexural plate wave sensor and array, and more particularly to a flexural plate wave sensor having reduced dimensions which enable the array to have an increased density of sensors on a single silicon wafer.

BACKGROUND OF INVENTION

Flexural plate wave (FPW) devices are gravimetric sensors capable of detecting mass changes as small as $10^{-11}$ g. Typically, FPW devices are built with a bulk micromachining process which produces a thin film membrane of silicon or silicon nitride by etching a cavity through the entire thickness of the silicon wafer with a selective process which does not attack the membrane material. However, due to the crystal structure of the silicon wafer, the cavity produced by this etching process has interior walls which extend through the silicon wafer at an angle of 126° from the membrane. This results in the cavity having an opening at the bottom surface of the substrate which is at least twice as large as the area of the membrane. Accordingly, the smallest possible FPW device built utilizing the prior art bulk micromachining process is approximately 1 mm×1 mm, since, for this one square millimeter of area on the surface of the silicon wafer, at least twice as much area is required on the bottom of the wafer. Therefore, only small numbers of FPW sensors can be integrated onto the same silicon chip for exposure to the same environment. For applications which require several sensors with different coatings, several packaged sensors must be integrated onto a sensor assembly and exposed to a gas or liquid sample stream. This method is only practical for applications requiring less than approximately 20 separate sensors.

SUMMARY OF THE INVENTION

It is therefore an object of this invention to provide a flexural plate wave sensor having reduced areal dimensions which enable an array of sensors to have an increased density of sensors on a single silicon wafer.

It is a further object of this invention to provide such a flexural plate wave sensor including a sensor membrane having increased sensitivity.

It is a further object of this invention to provide such a flexural plate wave sensor in which the sensor membrane is not sealed on one side, thereby eliminating atmospheric pressure variations in the membrane tension.

It is yet a further object of the invention to provide such a flexural plate wave sensor in which the absorptive coating is separate from the electrical components for sensing elements in fluid environments.

It is a yet further object of this invention to provide a flexural plate wave sensor array having increased packing density which enables a greater number of sensors to be fit on a single silicon chip.

It is a further object of this invention to provide a method of making a flexural plate wave sensor in which the sensor membrane is not exposed until the end of the manufacturing of the sensor.

This invention results from the realization that a truly effective flexural plate wave sensor can be obtained by bulk machining the silicon wafer to form a sensor having a cavity with substantially parallel interior walls, adding an etch stop layer and a membrane layer to the wafer, adding an absorptive coating on the membrane layer and transducers on the membrane layer opposite the absorptive coating. This construction facilitates the formation of an array of sensors having increased packing density on the silicon wafer.

This invention features a method for manufacturing a flexural plate wave sensor including the steps of depositing an etch-stop layer over a substrate, depositing a membrane layer over the etch stop layer, depositing a piezoelectric layer over the membrane layer, forming a first transducer on the piezoelectric layer and forming a second transducer on the piezoelectric layer, spaced from the first transducer. The method further includes the steps of etching a cavity through the substrate, the cavity having substantially parallel interior walls, removing the portion of the etch stop layer between the cavity and the membrane layer to expose a portion of the membrane layer, and depositing an absorptive coating on the exposed portion of the membrane layer.

In a preferred embodiment, the method may further include the steps of etching a hole in the piezoelectric layer and forming a ground contact on the silicon membrane layer.

This invention also features a flexural plate wave sensor including a base substrate, an etch stop layer disposed over the base substrate, a membrane layer disposed over the etch stop layer and a cavity having substantially parallel interior walls disposed in the base substrate and the etch stop layer, thereby exposing a portion of the membrane layer. The flexural plate wave sensor further includes an absorptive coating disposed on the exposed portion of the membrane layer within the cavity, a piezoelectric layer disposed over the membrane layer, a first transducer disposed on the piezoelectric layer, and a second transducer disposed on the piezoelectric layer, spaced from the first transducer.

In a preferred embodiment, the first and second transducers may be interdigitated transducers. The first and second transducers may be formed from TiPtAu or from aluminum. The piezoelectric layer may be formed from aluminum nitride, lead zirconium titanate or zinc oxide. The etch stop layer may be formed from silicon dioxide or from silicon and the base substrate may be formed from silicon.

This invention also features a method for manufacturing a flexural plate wave sensor including the steps of depositing a sacrificial material layer over a silicon substrate, depositing a membrane layer over the sacrificial material layer with the membrane layer covering the sacrificial material layer and contacting the silicon substrate and depositing a piezoelectric layer over the membrane layer. The method further includes forming a first transducer on the piezoelectric layer, forming a second transducer on the piezoelectric layer, spaced from the first transducer, removing the sacrificial material layer to expose a portion of the membrane layer and depositing an absorptive costing on the exposed portion of the membrane layer.

This invention also features a flexural plate wave sensor including a substrate, a membrane layer disposed on the substrate, the membrane layer having legs in contact with the substrate and a body portion spanning between the legs. The substrate, a lower surface of the body portion and interior surfaces of the legs define a cavity between the substrate and the body portion. The flexural plate wave sensor further includes an absorptive coating disposed on the lower surface of the body portion of the membrane layer, a piezoelectric layer disposed over an upper surface of the membrane material, a first transducer disposed on the piezoelectric layer and a second transducer disposed on the piezoelectric layer, spaced from the first transducer.

In a preferred embodiment, the substrate may be formed from silicon and the membrane layer may be formed from silicon. The first and second transducers may be interdigitated transducers that may be formed from TiPtAu or from aluminum. The piezoelectric layer may be formed from aluminum nitride, lead zirconium titanate or zinc oxide.

This invention also features a method for manufacturing a flexural plate wave sensor including the steps of depositing a membrane layer on a substrate having a concave upper surface, thereby forming a cavity between an exposed portion of the membrane layer and the substrate, depositing a piezoelectric layer on the membrane layer, forming a first transducer on the piezoelectric layer, forming a second transducer on the piezoelectric layer, spaced from the first transducer, and depositing an absorptive coating on the exposed portion of the membrane layer within the cavity.

This invention also features a flexural plate wave sensor including a substrate having a recess disposed in an upper surface thereof, a membrane layer disposed on the upper surface of the substrate, a cavity disposed between a portion of the membrane layer and the recess in the substrate and a piezoelectric layer disposed on the membrane layer. The flexural plate wave sensor further includes a first transducer disposed on the piezoelectric layer, a second transducer disposed on the piezoelectric layer, spaced from the first transducer and an absorptive coating disposed on the portion of the membrane layer within the cavity.

In a preferred embodiment, the substrate may be formed from a material selected from silicon or PYREX® material. The first and second transducers may be interdigitated transducers formed from TiPtAu or from aluminum. The piezoelectric layer may be formed from aluminum nitrate, lead zirconium titanate or zinc oxide.

This invention also features a flexural plate wave sensor array including a substrate, and a plurality of flexural plate wave sensors. Each sensor includes a cavity formed in the substrate, a thin film membrane layer spanning the cavity, a piezoelectric layer disposed on the thin film membrane layer, a transducer disposed on the piezoelectric layer and an absorptive coating disposed on the thin film membrane layer within the cavity. The cavity of each of the sensors includes interior walls that are substantially parallel to each other and to the interior walls of adjacent sensors.

This invention also features a flexural plate wave sensor array including a substrate and a plurality of flexural plate wave sensors. Each sensor includes a cavity formed in the substrate, a thin film membrane layer spanning the cavity, a piezoelectric layer disposed on the thin film membrane layer, a transducer disposed on the piezoelectric layer and an absorptive coating disposed on the thin film membrane layer within the cavity. The distance between adjacent sensors is no greater than 0.9 mm.

This invention also features a flexural plate wave sensor array including a substrate, a plurality of flexural plate wave sensors, each sensor including a cavity formed in the substrate, a thin film membrane layer spanning the cavity, a piezoelectric layer disposed on the thin film membrane layer, a transducer disposed on the piezoelectric layer and an absorptive coating disposed on the thin film membrane layer within said cavity; a reference flexural plate wave sensor including a cavity formed in the substrate, a thin film membrane layer spanning the cavity, a piezoelectric layer disposed on the thin film membrane layer and a transducer disposed on the piezoelectric layer; and a microprocessor electrically connected to each of the plurality of flexural plate wave sensors and the reference flexural plate wave sensor, for monitoring resonant frequency characteristics of the sensors.

In a preferred embodiment, the reference sensor may monitor the effects of environmental factors on the sensors and the microprocessor adjusts the resonant frequency of the sensors to compensate for the environmental factors.

This invention also features a flexural plate wave sensor array including a substrate and a plurality of flexural plate wave sensors, each sensor including a cavity formed in the substrate, a thin film membrane layer spanning the cavity, a piezoelectric layer disposed on the thin film membrane layer, a transducer disposed on the piezoelectric layer and a plurality of discrete absorptive coatings disposed on the thin film membrane layer within the cavity. The cavity of each of the sensors includes interior walls which are substantially parallel to each other and to the interior walls of adjacent sensors.

This invention also features a flexural plate wave sensor array including a substrate; a plurality of flexural plate wave sensors, each sensor including a cavity formed in the substrate, a thin film membrane layer spanning the cavity, a piezoelectric layer disposed on the thin film membrane layer, a transducer disposed on the piezoelectric layer and an absorptive coating disposed on the thin film membrane layer within the cavity; a drive amplifier which receives a drive input and outputs an amplified drive output; a multiplexer which receives the amplified drive output and a selection signal, for driving one of the plurality of flexural plate wave sensors; and an output amplifier which senses an output from the one of the plurality of flexural plate sensors and outputs an amplified sensed signal.

BRIEF DESCRIPTION OF THE DRAWINGS

Other objects, features and advantages will occur to those skilled in the art from the following description of a preferred embodiment and the accompanying drawings, in which.

DISCLOSURE OF THE PREFERRED EMBODIMENT

Flexural plate wave (FPW) sensors are used to sense pressure, acceleration, density of liquids, viscosity of liquids, to detect chemical vapors and to detect biochemical interactions. The surface micromachined FPW sensor includes a thin film membrane, a piezoelectric layer over the membrane, an input interdigitated transducer (IDT) disposed on the piezoelectric layer adjacent a first section of the membrane and an output IDT disposed on the piezoelectric layer adjacent a second section of the membrane. The input IDT responds to an input via piezoelectric transduction to send an acoustic plate wave across the membrane where it is received by the output IDT where piezoelectric transduction creates an output. The velocity of the acoustic plate wave is dependent upon the membrane material and the mass per unit area of the membrane. The exposed portion of the membrane is coated with an absorptive coating in order to provide an indication of the detection of an analyte. Different absorptive coatings may be used in an array to detect different substances. The change of the mass per unit area caused by the absorption of an analyte by the absorptive coating on the membrane provides a shift in velocity of the acoustic plate wave sent across the membrane from the input IDT to the output IDT and a concomitant frequency shift. The shift in frequency is detected, indicating that the target chemical vapor or substance has been detected by the sensor.

Figure 1A:
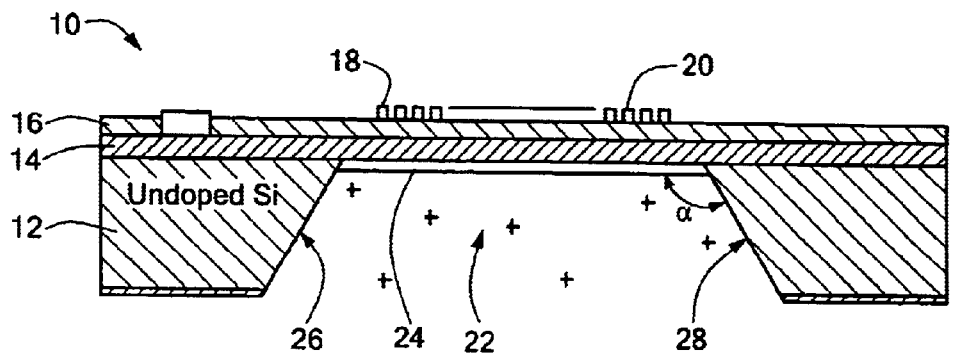
FIG. 1A is a cross-sectional side view of a prior art bulk machined flexural plate wave sensor.
Figure 1B:
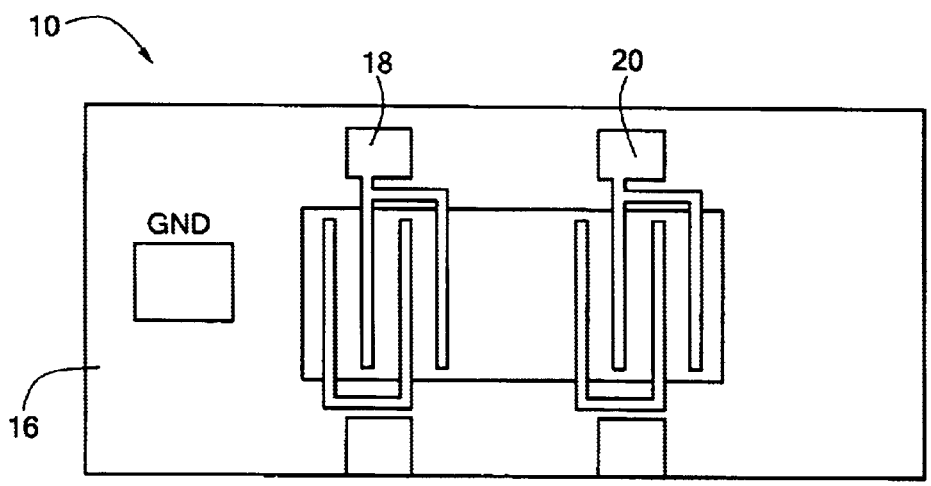
FIG. 1B is a top view of the prior art bulk machined flexural plate wave sensor.

A prior art bulk micromachined FPW device 10 is shown in FIGS. 1A and 1B. The FPW device 10 includes a substrate 12 of undoped silicon. A layer of membrane material 14 is deposited on a surface of the silicon substrate 12. A piezoelectric layer 16 is deposited on the layer of membrane material 14. An input IDT 18 is disposed on the piezoelectric layer of material 16 proximate a first portion of the membrane layer 14 and an output IDT 20 is disposed on the piezoelectric layer 16 proximate a second portion of the membrane layer 14.

Utilizing bulk micromachining techniques, a cavity 22 is etched into the silicon substrate 12 such that a section of the membrane layer 14 is exposed. The exposed section of the membrane layer 14 is coated with an absorptive coating 24 such that absorption by the absorptive coating 24 the target substance is detected by the device 10. However, physical limitations of the bulk micromachining process in the formation of cavity 22 results in the cavity having interior walls 26 and 28 which are formed at an angle α of 126°. Accordingly, due to the aspect ratio of the height relative to the width of the cavity 22 etched into the silicon substrate, the size of the membrane layer 14 can be no smaller than approximately 1 mm×1 mm, and the minimum spacing between adjacent sensors in an array can be no less than approximately 1 mm.

Given the size limitation of the exposed surface of the membrane layer, in order to detect a large number of components of a gas or liquid stream, a large number of sensors must be provided. The physical size of a sensor assembly incorporating a large number of sensors must also be large in order to provide detailed analyses of the fluid being tested. Accordingly, detailed analysis of a sample becomes cumbersome and difficult to manage since there are multiple large sensors, each of which must be exposed to the same liquid or gas sample.

Figure 2A:
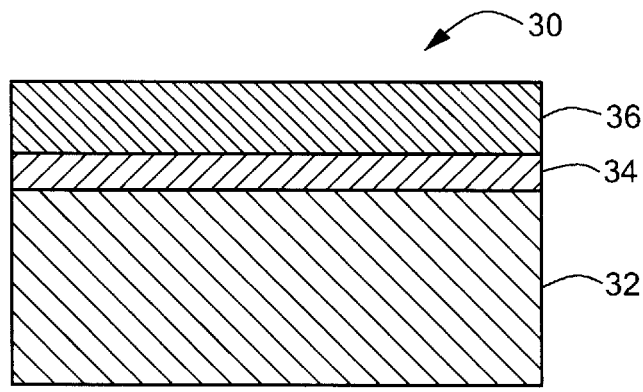
FIGS. 2A–2G are cross-sectional side views showing the steps involved in the method of manufacturing the flexural plate wave sensor in accordance with the present invention.
Figure 2B:
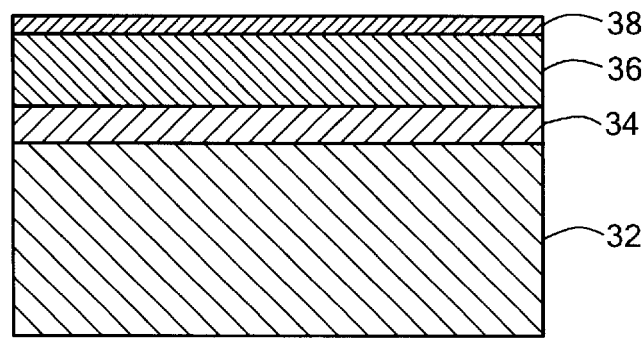
Figure 2C:
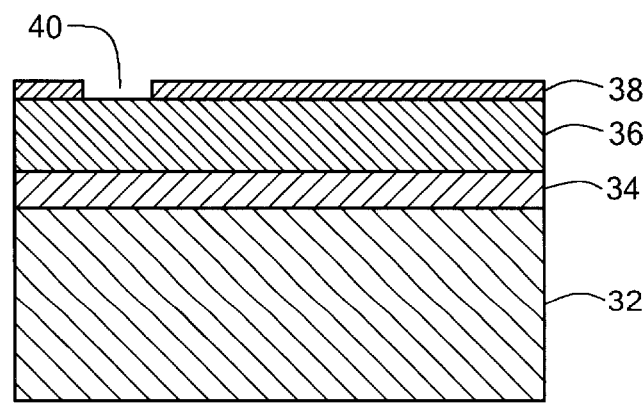
Figure 2D:
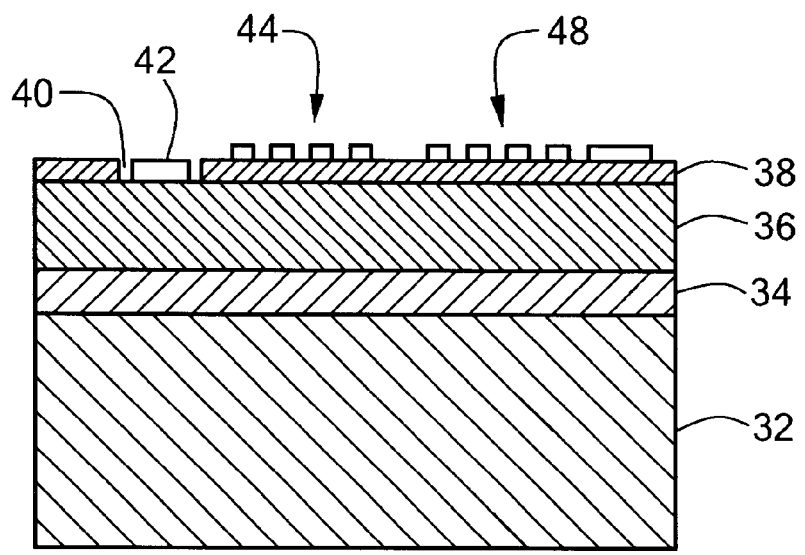
Figure 2E:
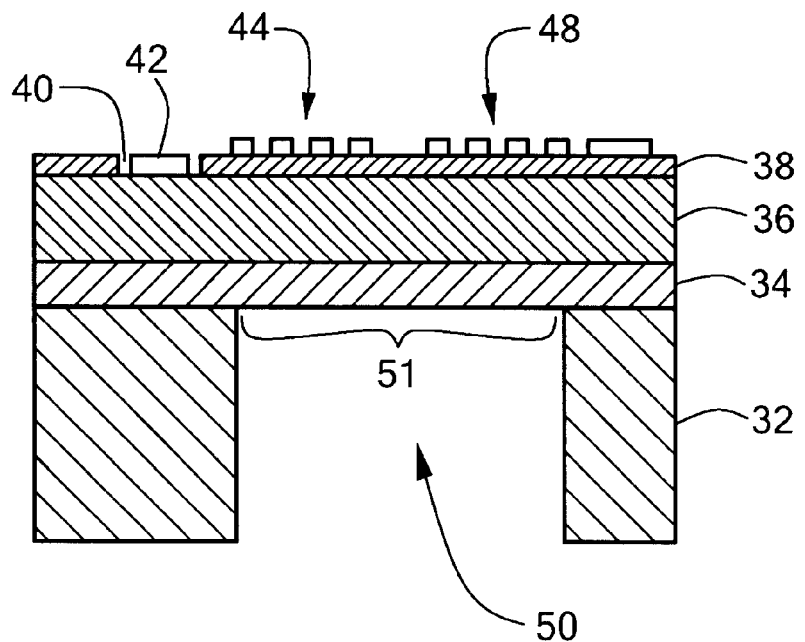
Figure 2F:
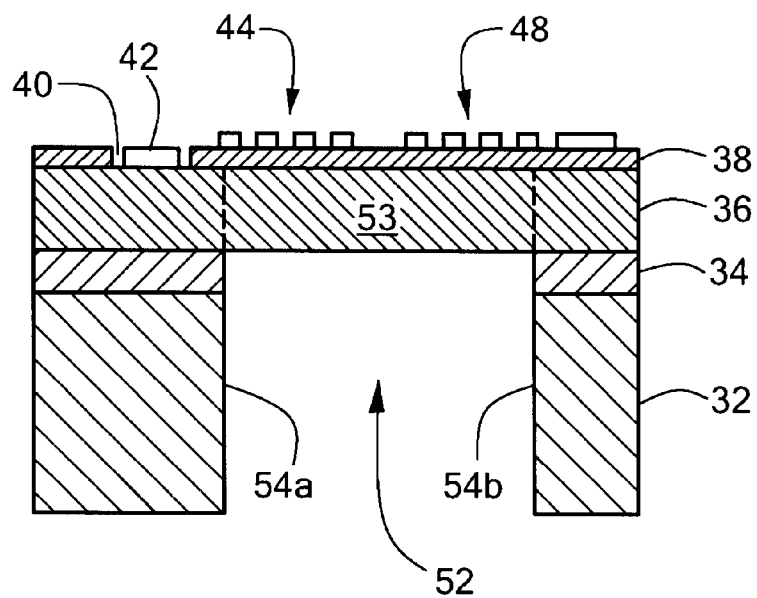
Figure 2G:
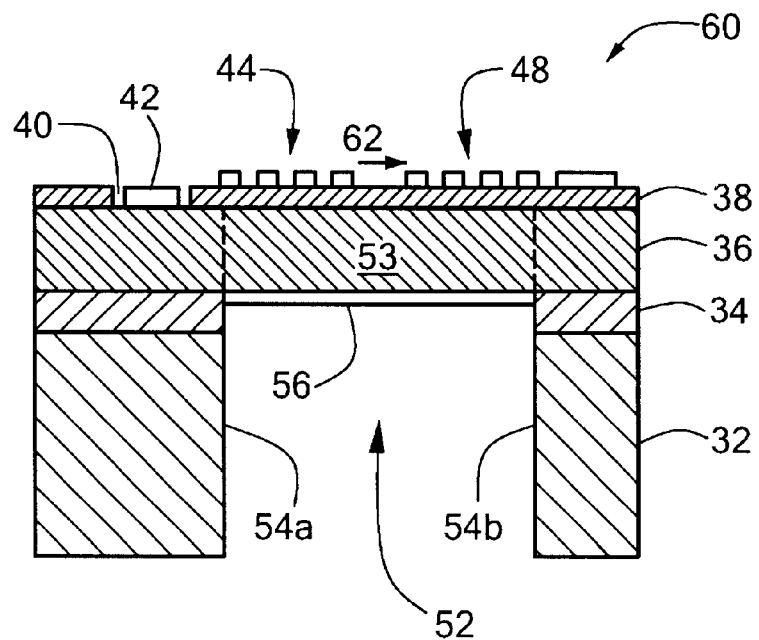

FIGS. 2A–2G illustrate the steps involved in the method of manufacturing the flexural plate wave sensor in accordance with the present invention. Shown in FIG. 2A is a silicon-on-insulator (SOI) wafer 30, which includes a silicon substrate 32, a silicon dioxide etch stop layer 34 on the silicon substrate 32 and a silicon membrane layer 36 on the silicon dioxide etch stop layer 34. In the preferred embodiment, the silicon substrate 32 is approximately 400 microns thick, the silicon dioxide etch stop layer 34 is 1 micron thick and the silicon membrane layer 36 is 2 microns thick. It is a portion of this silicon layer 36 which, in the finished sensor shown in FIG. 2G, is the thin film membrane through which the acoustic plate wave is transmitted.

A piezoelectric layer 38, FIG. 2B, is then applied to the upper surface of the silicon membrane layer 36. Piezoelectric layer 38 has a thickness of 0.5 microns and can be formed from any piezoelectric material, such as aluminum nitride or zinc oxide. A hole 40, FIG. 2C, is then etched into the piezoelectric layer 38 to the surface of the silicon membrane layer 36. A ground terminal 42, FIG. 2D, is deposited in the hole 40, in contact with the silicon layer 36, and input IDT 44 and output IDT 48 are deposited on piezoelectric layer 38. Ground terminal 42, input IDT 44 and output IDT 48 are preferably formed from a 0.1 micron thick layer of TiPtAu metal. Alternatively, ground terminal 42, IDT 44 and IDT 48 may be formed from aluminum. Using an inductively coupled plasma (ICP) etch machine, a cavity 50, FIG. 2E, is etched into the silicon substrate 32 up to, but not including the silicon dioxide etch stop layer 34, which acts as an etch stop for the ICP process. The exposed portion 51 of the silicon dioxide etch stop layer 34 is then removed by dipping the portion 51 into buffered hydrofluoric acid, thereby exposing a portion of the silicon layer 36 to form thin film membrane 53. As shown in FIG. 2F, the resulting sensor 60 includes a cavity 52 having interior walls 54*a* and 54*b* which are much less than 126°: they are substantially parallel to each other. An absorptive coating 56, FIG. 2G, is then applied to the exposed surface of thin film membrane 53 of silicon layer 36.

In operation, the input IDT 44 transmits an acoustic plate wave across the thin film silicon membrane 53 in the direction of arrow 62, where it is received by the output IDT 48. As long as the absorptive coating 56 does not absorb any of the target substance, the mass per unit area of the membrane 36 remains constant, resulting in a constant frequency of the acoustic plate wave. However, as the absorptive coating 56 absorbs the target substance, the mass per unit area of the membrane increases. This results in a shift in the velocity of the acoustic plate wave and, consequently, a frequency shift in the wave received by the output IDT 48. This frequency shift is recognized as an indication that the target substance has been detected by the sensor 60. Alternatively, more than one type of absorptive coating 56, 56' may be applied to the membrane 53 of each sensor. See FIGS. 2G and 2H. This enables each sensor to detect different analytes which may be absorbed by the different coatings.

Figure 3:
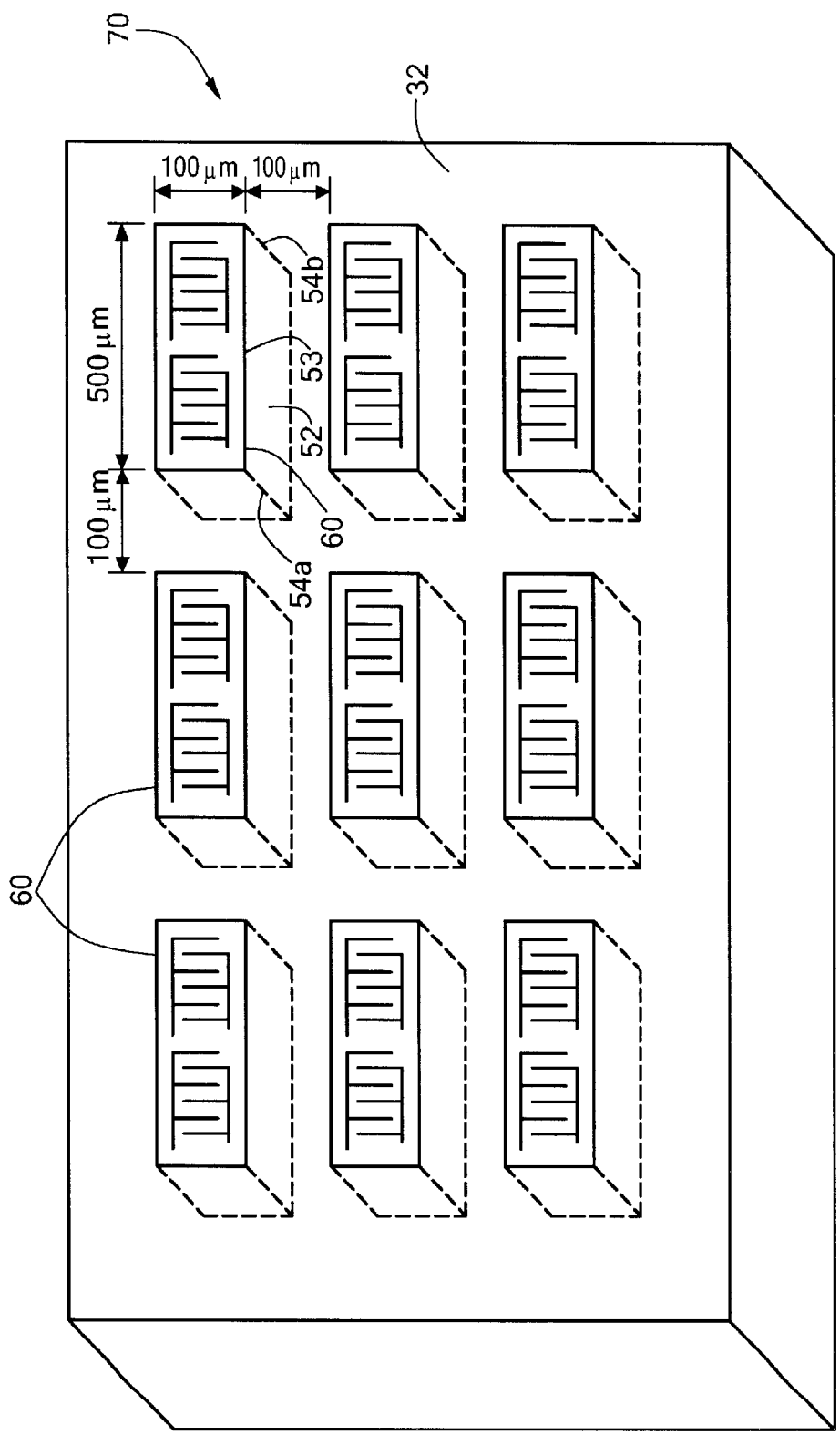
FIG. 3 is a schematic diagram of a flexural plate wave sensor array in accordance with the present invention.

An array 70 of flexural plate wave sensors 60 is shown in FIG. 3. Due to the process described above with reference to FIGS. 2A–2G, the resulting sensor 60 can be made as small as approximately 500 microns by 100 microns. Furthermore, since the interior walls 54*a* and 54*b* of cavity 52 are substantially parallel to each other and to the interior walls of adjacent sensors, these sensors can be more densely packed onto the substrate 32. As shown in FIG. 3, the spacing between adjacent sensors 60 can be as little as 100 microns. This configuration enables an increased number of sensors 60 to be fit onto a single silicon wafer, thereby enabling a increased number of substances to be detected with the use of a single silicon chip.

Figure 4A:
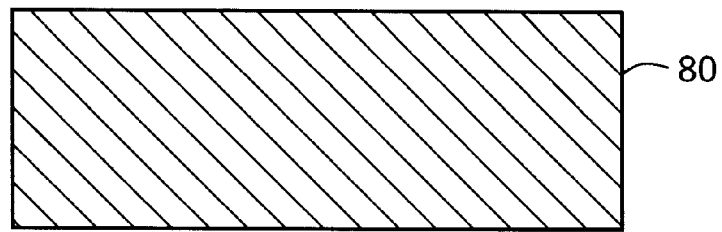
FIGS. 4A–4F are cross-sectional side views showing the steps involved in the method of manufacturing a second embodiment of the flexural plate wave sensor of the present invention.
Figure 4B:
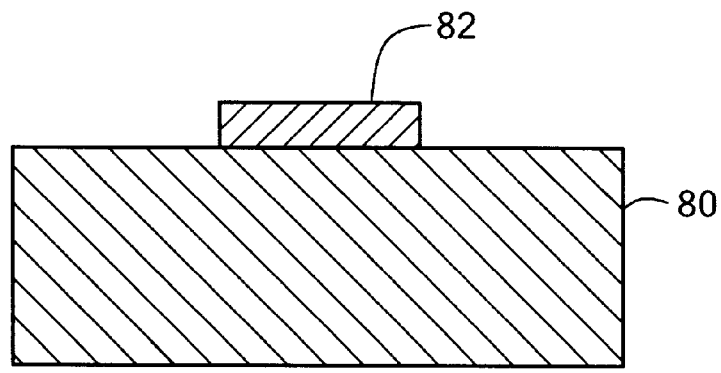
Figure 4C:
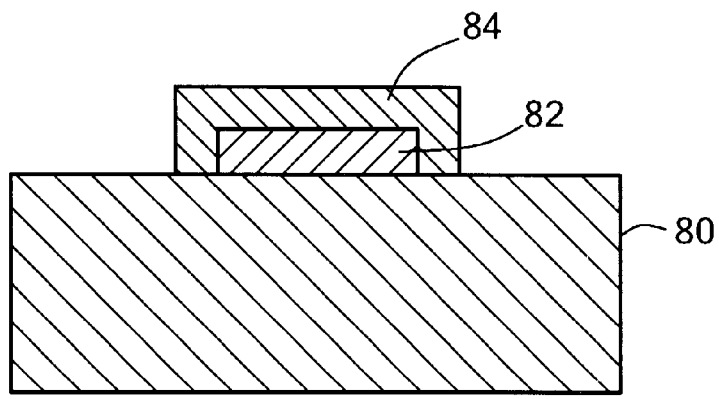
Figure 4D:
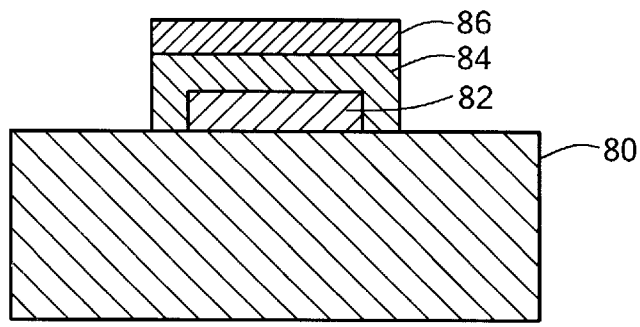
Figure 4E:
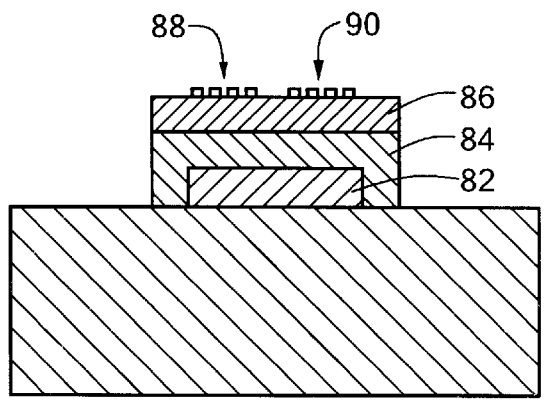
Figure 4F:
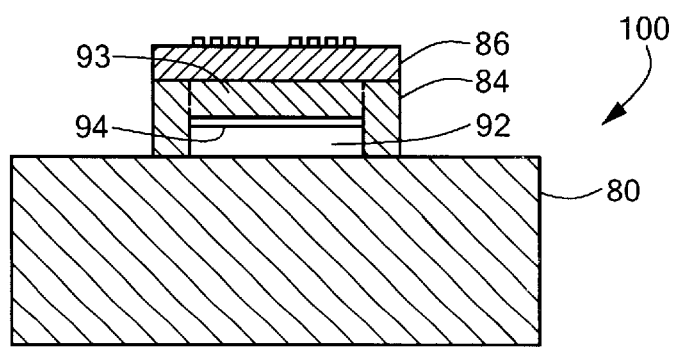

The steps involved in the method of making a second embodiment of the flexural plate wave sensor are illustrated in FIGS. 4A–4F. The process begins with a silicon substrate 80, FIG. 4A on which a sacrificial layer of material 82 is deposited, FIG. 4B. The sacrificial layer 82 is any material that can be easily removed from the substrate 80, such as glass or a photoresistive material. A structural layer 84 is deposited over the sacrificial layer 82, FIG. 4C. The structural layer 84 covers the top and sides of the sacrificial layer 82 and contacts the substrate 80. Piezoelectric layer 86 is deposited over the structural layer 84, FIG. 4D. An input IDT 88 and an output IDT 90 are then deposited on the piezoelectric layer 86, FIG. 4E. The sacrificial layer 82 is then etched away to create a cavity 92 with a thin film membrane 93 disposed between the cavity 92 and the piezoelectric layer 86. An absorptive coating 94 is then deposited on the exposed surface of the thin film membrane 93, FIG. 4F. The resulting sensor 100, FIG. 4F is sized similarly to the sensor 60, FIG. 2G, and operates in the same manner.

Figure 5:
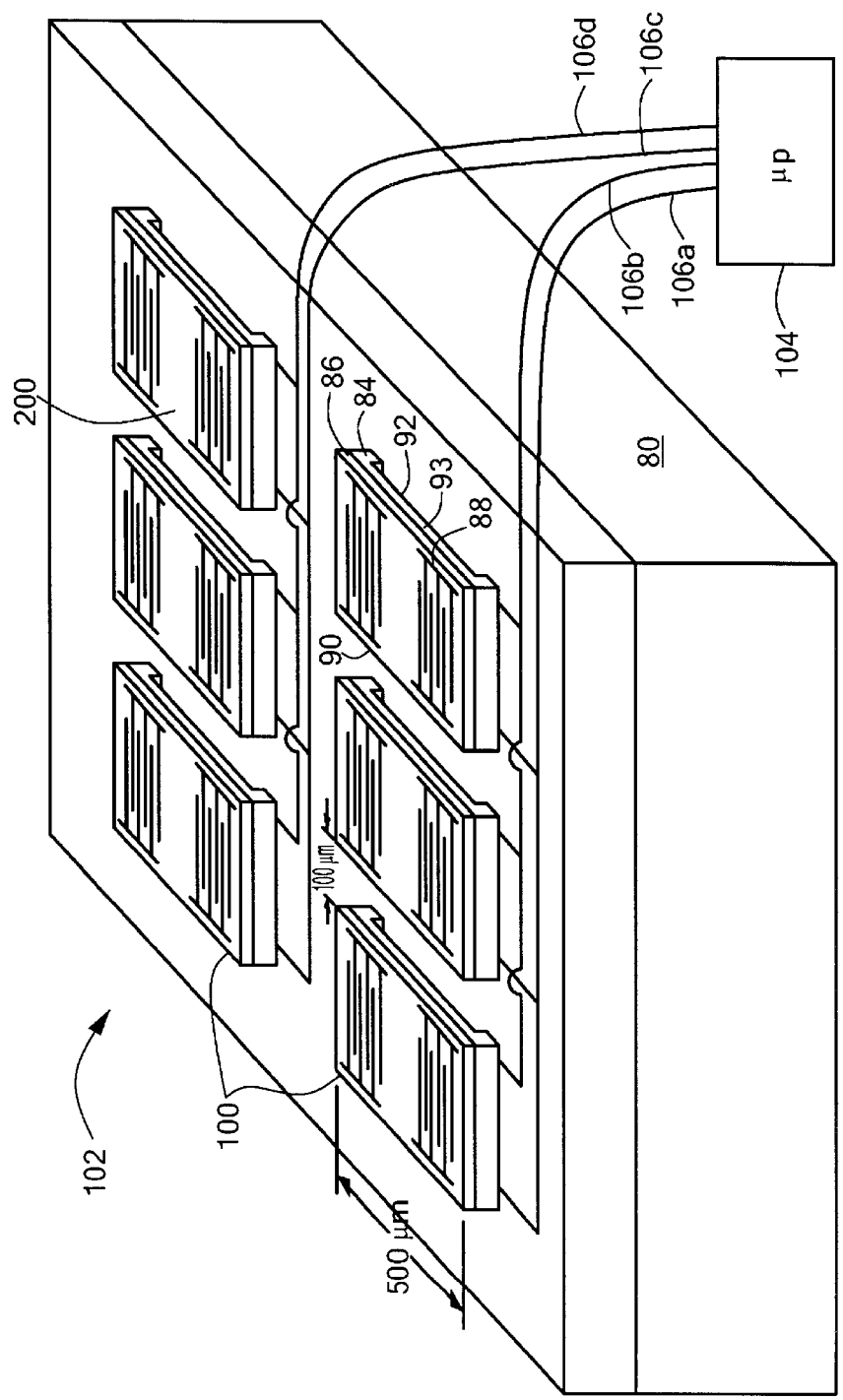
FIG. 5 is a schematic diagram of a flexural plate wave sensor array in accordance with the second embodiment of the present invention.

An array 102 of sensors 100 is shown in FIG. 5, where it can be seen that, due to this particular method of manufacturing, with the shallower angled sides on the cavity, the sensors 100 require as little as 100 microns between adjacent sensors, thereby increasing the packing density of the array 102.

A reference sensor 200, which is formed identically to sensors 100, but does not include the absorbtive coating, is used to monitor the effects of environmental factors, such as temperature and pressure on the resonant frequency characteristics of the sensors 100. Each of the sensors 100 and sensor 200 is connected to a microprocessor 104 via lines 106a–106d. Microprocessor 104 monitors the resonant frequency characteristic of sensors 100 and 200 independently, so that environmental factors as sensed by sensor 200 can be compensated for.

Figure 7:
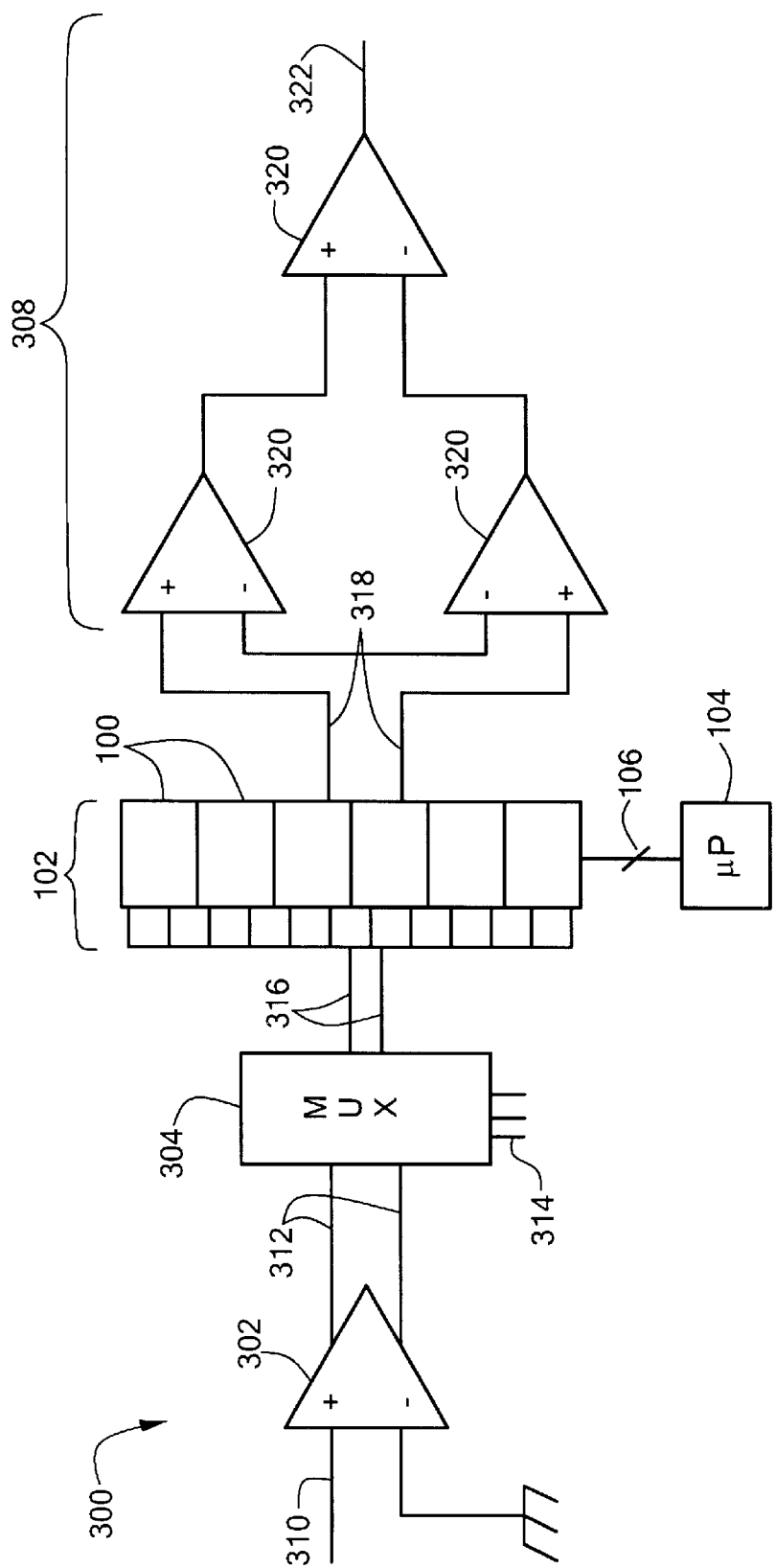
FIGS. 7 is a schematic diagram of the input and output circuitry of a flexural plate wave sensor array in accordance with the present invention.

The sensor input and output circuitry for the sensor array 102 and generally shown at 300 in FIG. 7. Circuitry 300 includes a drive amplifier 302 which is a high-again single-ended input-to-differential output amplifier, which receives an input on line 310 and outputs a differential signal on lines 312. Multiplexer 304 receives the differential outputs on lines 312 and, based on a selection signal present on lines 314, selects one of the n sensors 100 of array 102 to activate by providing a differential drive signal to the selected sensor 100 on lines 316. The differential output of the selected sensor 100 is input to amplifier section 308 on lines 318. Amplifier section 308 includes high-again amplifiers 320 that are configured as an instrumentation amplifier. This configuration allows for symmetrical loading on each sensor output, high common-mode signal rejection, and higher gains for a given limited bandwidth. Amplifier section 308 outputs the amplified sensor output on line 322. This configuration enables a single input/output device to drive and monitor an array of sensors. The multiplexer 304 can be operated to cycle through each sensor in the array. Accordingly, an array having a number n of sensors, each having a different absorbtive coating for detecting different analytes, can be driven with a single input/output device which cycles through the sensors for detecting the presence of a number of analytes.

Figure 6A:
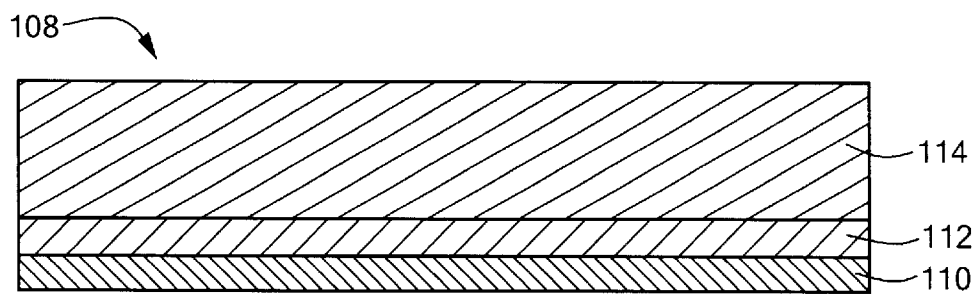
FIGS. 6A–6G are cross-sectional side views showing the steps involved in the method of manufacturing a third embodiment of the flexural plate wave sensor according to the present invention.
Figure 6B:
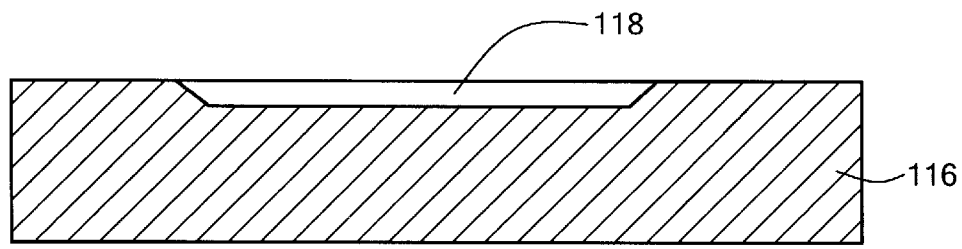
Figure 6C:
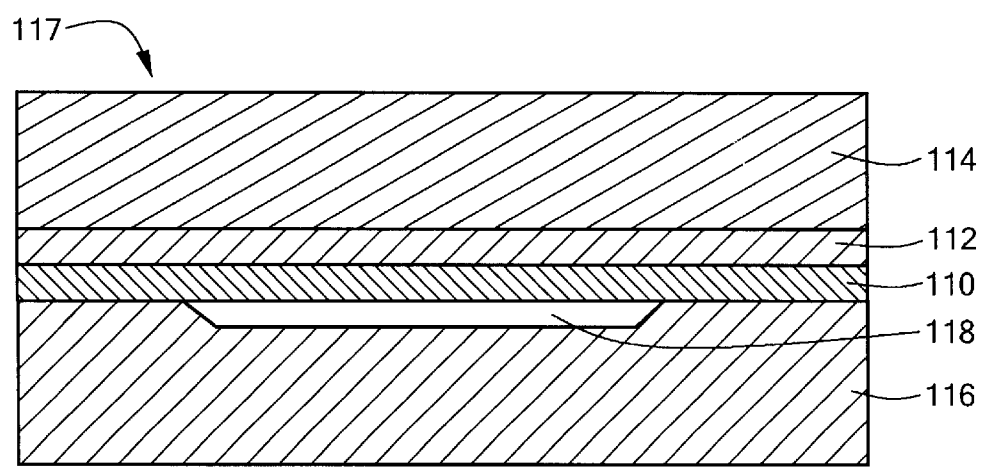
Figure 6D:
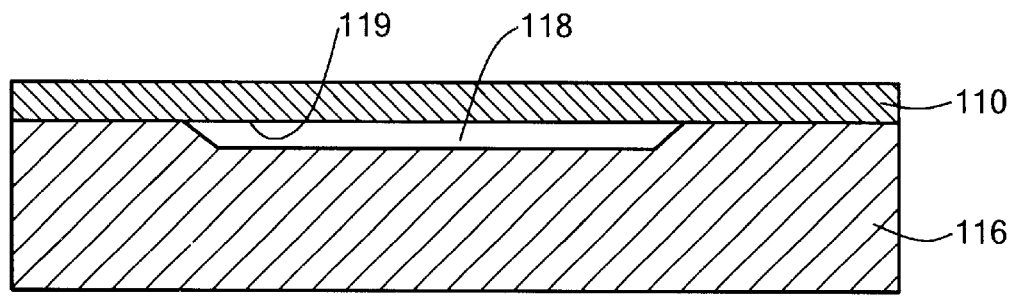
Figure 6E:
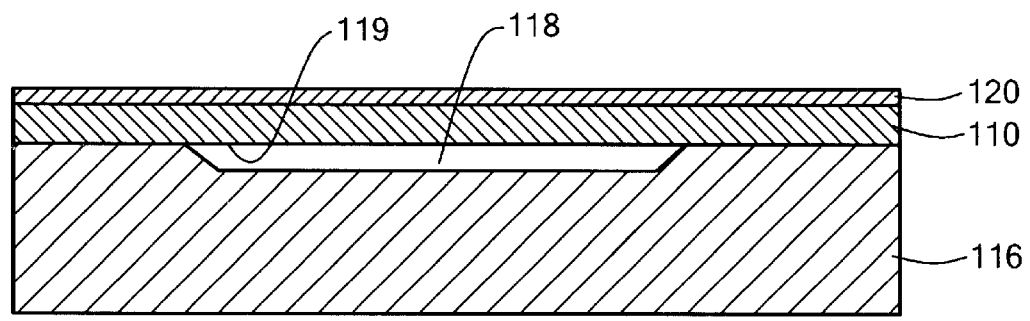
Figure 6F:
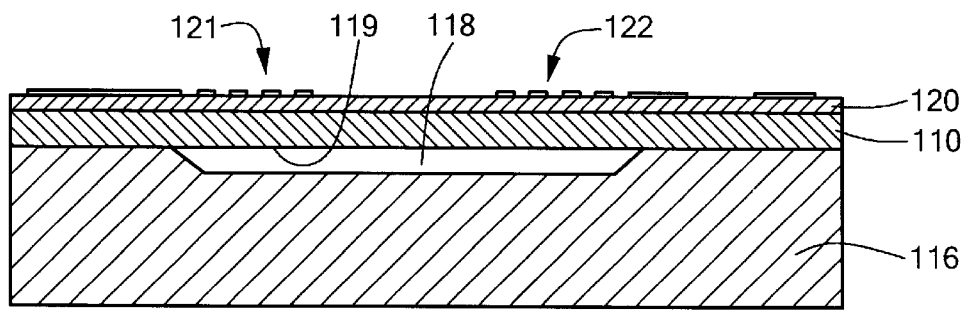
Figure 6G:
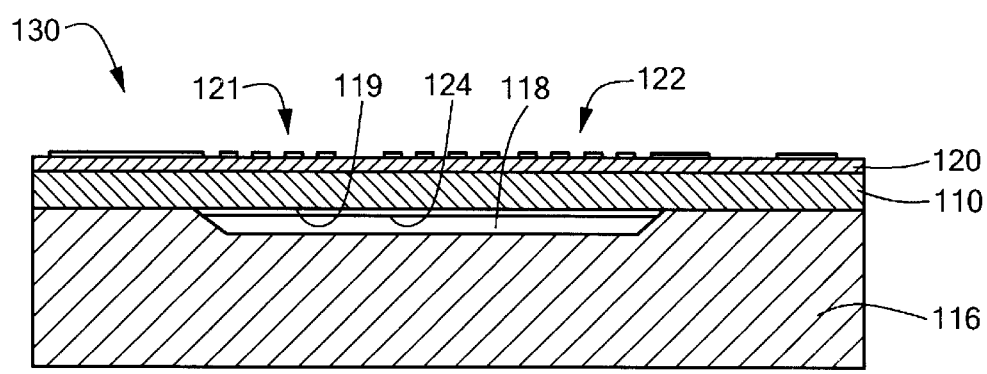

FIGS. 6A–6G illustrate the steps involved in the method of making a third embodiment of the flexural plate wave sensor. First, a silicon-on-insulator layer 108, including a silicon layer 110, a silicon dioxide layer 112 and a silicon handle wafer 114, FIG. 6A is deposited on a substrate 116. The substrate 116 may be formed from PYREX® brand glass from Corning or silicon, and has a cavity 118 disposed on an upper surface thereof, FIG. 6B. The resulting structure 117 is shown in FIG. 6C. The silicon handle wafer 114 and silicon dioxide layer 112 are then etched away, leaving the silicon layer exposed, thereby forming a thin film membrane 119 over the cavity 118, FIG. 6D. A piezoelectric layer 120 is then deposited over the silicon layer 110, FIG. 6E. An input IDT 120 and an output IDT 122 are then formed on the piezoelectric layer 120 over the silicon membrane 119, FIG. 6F. Finally, an absorptive coating 124 is deposited over the bottom surface of the silicon membrane 119 to form the flexural plate wave sensor 130, FIG. 6F. The sensor 130 is sized similarly to the sensor 60, FIG. 2G, and operates in the same manner.

It can therefore be seen, that, due to the manufacturing processes involved in fabricating the flexural plate wave sensors of the present invention, the size of the membrane can be greatly reduced compared to prior art sensors. This reduction in the size of the thin film membrane allows the thickness of the thin film membrane to be greatly reduced. Since the sensitivity of the sensor is inversely proportional to the mass per unit area of the thin film membrane, a membrane which is ten times thinner than a prior art sensor is consequently ten times more sensitive than the prior art sensor. Furthermore, as described above, the reduction in the area of the sensors combined with the feature of the substantially parallel interior walls of the cavities of the sensors allows a greater packing density of the sensors, resulting in a greater number of sensors being disposed on a single silicon chip.

The FPW sensors produced by the above described methods have numerous applications, including a gas analyzer device capable of detecting the presence and concentration of hundreds of molecular components with less than one part per billion minimum detectable concentration sensitivity. The FPW sensor could be incorporated into a liquid analyzing device capable of analyzing samples for several hundred possible contaminants or components simultaneously. The FPW sensor could also be utilized as part of a DNA sequencing device, as a virus/antibody detection device and for biological weapon detection.

Although specific features of the invention are shown in some drawings and not in others, this is for convenience only as each feature may be combined with any or all of the other features in accordance with the invention.

Other embodiments will occur to those skilled in the art and are within the following claims:

What is claimed is:

1. A method for manufacturing a flexural plate wave sensor comprising the steps of:

depositing a sacrificial material layer over a silicon substrate;

depositing a membrane layer over the sacrificial material layer with said membrane layer covering said sacrificial material layer and contacting said silicon substrate;

depositing a piezoelectric layer over said membrane layer;

forming a first transducer on said piezoelectric layer;

forming a second transducer on said piezoelectric layer, spaced from said first transducer;

removing said sacrificial material layer to expose a portion of said membrane layer; and depositing an absorptive coating on said exposed portion of said membrane layer.

2. A flexural plate wave sensor comprising:

a substrate;

a membrane layer disposed on said substrate, said membrane layer having legs in contact with said substrate and a body portion spanning between said legs, wherein said substrate, a lower surface of said body portion and interior surfaces of said legs define a cavity between said substrate and said body portion;

an absorptive coating disposed on the lower surface of said body portion of said membrane layer;

a piezoelectric layer disposed over an upper surface of said membrane layer;

a first transducer disposed on said piezoelectric layer, and a second transducer disposed on said piezoelectric layer, spaced from said first transducer.

3. The flexural plate wave sensor of claim 2 wherein said substrate is formed from silicon.

4. The flexural plate wave sensor of claim 2 wherein said membrane layer is formed from silicon.

5. The flexural plate wave sensor of claim 2 wherein said first and second transducers are interdigitated transistors.

6. The flexural plate wave sensor of claim 2 wherein said first and second transducers are formed from TiPtAu.

7. The flexural plate wave sensor of claim 2 wherein said first and second transducers are formed from aluminum.

8. The flexural plate wave sensor of claim 2 where said piezoelectric layer is formed from material selected from the group consisting of aluminum nitride, zinc oxide, and lead zirconium titanate.

* * * * *